(12) United States Patent
Hirsch

(10) Patent No.: US 8,357,404 B2
(45) Date of Patent: Jan. 22, 2013

(54) METHOD OF ALTERING PERCEPTION OF TIME

(76) Inventor: Alan R. Hirsch, Riverwoods, IL (US)

(*) Notice: Subject to any disclaimer, the term of this patent is extended or adjusted under 35 U.S.C. 154(b) by 57 days.

(21) Appl. No.: 13/004,296

(22) Filed: Jan. 11, 2011

(65) Prior Publication Data

US 2011/0171131 A1 Jul. 14, 2011

Related U.S. Application Data

(60) Provisional application No. 61/294,804, filed on Jan. 13, 2010.

(51) Int. Cl.
*A01N 65/00* (2009.01)
(52) U.S. Cl. .................................................. 424/725
(58) Field of Classification Search .................. None
See application file for complete search history.

(56) References Cited

U.S. PATENT DOCUMENTS

| | | | |
|---|---|---|---|
| 4,576,484 A | 3/1986 | Grossmeyer |
| 5,380,765 A | 1/1995 | Hirsch |
| 5,492,934 A | 2/1996 | Hirsch |
| 5,759,521 A | 6/1998 | Hirsch |
| 5,885,614 A | 3/1999 | Hirsch |
| 5,904,916 A | 5/1999 | Hirsch |
| 6,106,837 A | 8/2000 | Hirsch |
| 6,769,428 B2 | 8/2004 | Cronk et al. |
| 6,803,987 B2 | 10/2004 | Manne |
| 7,067,162 B1 | 6/2006 | Hirsch |
| 7,108,872 B1 | 9/2006 | Hirsch |
| 7,820,208 B2 | 10/2010 | Hirsch |
| 7,838,486 B2 | 11/2010 | Hirsch |
| 2003/0147938 A1 | 8/2003 | Hirsch |
| 2004/0137086 A1 | 7/2004 | Hirsch |
| 2006/0057232 A1 | 3/2006 | Hirsch |
| 2009/0123524 A1 | 5/2009 | Hirsch |
| 2009/0123579 A1 | 5/2009 | Hirsch |
| 2011/0064672 A1 | 3/2011 | Hirsch |

OTHER PUBLICATIONS

J.F.Gent et al, in Clinical Measurement of Taste and Smell, pp. 107-116, H.L. Meiselman, et al.(eds.), 602 pp., MacMillan, NY (1986).
R.L. Doty, et al. The American Neurological Association; "The Olfactory and Cognitive Deficits of Parkinson's Diesease: Evidence for Independence"; vol. 25: pp. 166-171 (1989).
E. Koss, et al., Neurology, Olfactory Detection and Identification Performance are Dissociated in early Alzheimer's Disease, vol. 38: pp. 1228-1232.
R. Doty, The Smell Identification Test: Administration Manual 1983; Philadelphia: Sensonics, Inc. (1983); 25 pages.
Amoore and O'Neill "Proposal for Unifying Scale to Express Olfactory Thresholds and Odor Levels: The "Decismel Scale"," in Proceedings of the 1988 Air Pollution Control Association Annual Meeting, Paper No. 78.5 (11 pp), Air and Waste Management Association, Pittsburg, PA (1988).
Amoore and Haotala, "Odor as an Aid to Chemical Safety: Odor Thresholds Compared with Threshold Limit Values and Volatilities for 214 Industrial Chemicals in Air and Water Dilution," J. Appl. Toxicology 3(6): 272-290 (1983).
UniSci—Daily University Science News, "Brain Areas Critical to Human Time Sense Identified", Feb. 27, 2001; 3 pages, downloaded Jan. 5, 2010 from www.unisci.com/stories/20011/0227013.htm.
G.Koch et al, Abstract for "Brief Communications—High frequency rTMS improves time perception in Parkinson disease", (Neurology 2004; 63:2405-2406); 2 pages, downloaded Jan. 5, 2010 from www.neurology.org/cgi/content/abstract/63/12/2405.
Graber et al, Abstract for "Speech perception deficits in Parkinson's disease: underestimation of time intervals compromises identification of durational phonetic contrasts" (Brain and Language 82(1):65-74, 2002), 3 pp.; downloaded Jan. 5, 2010 at http://www.sciencedirect.com/science?_ob=ArticleURL&_udi=B6WC0-460H779-7&_user=10&_coverDate=07%2F02%2F2002&_rdoc=1&_fmt=high&_orig=gateway&_origin=gateway&_sort=d&_docanchor=&view=c&_searchStrId=169839.
A.R.Hirsch et al, Chemical Senses, vol. 17, No. 5, Oct. 1992, pp. 643 & 643-4.
A.R.Hirsch et al, Chemical Senses, vol. 18, No. 5, Oct. 1993; Validation of the Chicago Smell Test (CST) in subjective normosmic neurologic patients; 1 page.

*Primary Examiner* — Michael Meller
(74) *Attorney, Agent, or Firm* — Whyte Hirschboeck Dudek SC

(57) ABSTRACT

Methods and compositions for modifying an individual's perception of an interval of time are disclosed.

2 Claims, 1 Drawing Sheet

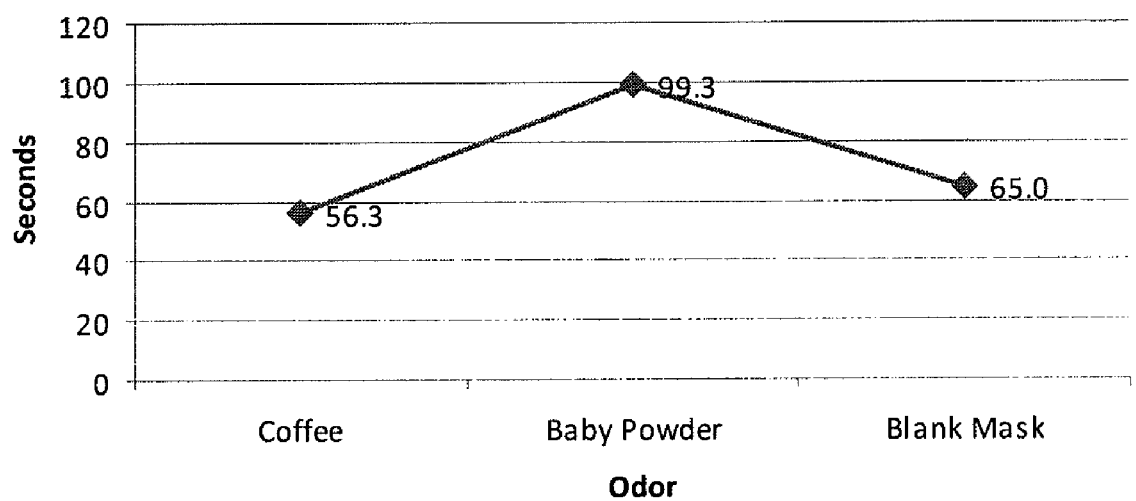

METHOD OF ALTERING PERCEPTION OF TIME

CROSS REFERENCE TO RELATED APPLICATION

This application claims priority under 35 U.S.C. §119(e) to Provisional Patent Application Ser. No. 61/294,804, filed on Jan. 13, 2010, the entire disclosure of which is hereby incorporated by reference.

FIELD OF THE INVENTION

Embodiments of the invention relate to altering an individual's perception of time, particularly duration of time, by the administration of odorants to the individual.

BACKGROUND OF THE INVENTION

Horology or the study of time is only in a primordial state. The workings of the internal biological clock have been explored with regard to physiological cyclical activities including wakefulness, nasal engorgement, and cognitive functioning as well as pathological states such as insomnia, epilepsy, migraine headaches, and defective perception of time in patient's suffering with Korsakoffs psychosis and Parkinson's disease such as underestimation of the duration of time.

The ability for timekeeping and making accurate decisions regarding the duration of time intervals is important in daily life. Sensorial influences on cognitive understanding of duration of time have remained in the development stage, mainly focusing on visual and auditory stimuli. It would be useful to provide a means of altering an individual's perception of time duration that is non-invasive, convenient, safe, and easy to administer.

BRIEF DESCRIPTION OF THE DRAWINGS

FIG. 1 is a graphical illustration of the mean values of the perceived time in seconds of the 60-second period for the two odorants and control across the 20 subjects of the Example.

DESCRIPTION OF THE INVENTION

The present invention relates to methods of using odorants to alter an individual's subjective perception of the length of an interval of time (time duration) (i.e., the length of a given time period as it is perceived or estimated) by the administration of a composition comprising an odorant or mixture of odorants for inhalation by an individual into the nasal passageway. In particular, the method involves delivering an effective amount or concentration of an odorant or mixture of odorants to an individual for inhaling to modify their judgment or estimation of a time interval compared to their judgment or estimation of the same time interval without inhaling the odorant or odorant mixture. The method is useful, for example, to promote distortions in time perception in an individual. The method can be utilized with both male and female individuals.

In some embodiments, a composition composed of an effective amount of an odorant or mixture of odorants can be administered for inhalation to an individual who has a normal perception of time to cause their perception of time to be abnormal such that the individual perceives a time period a) to be less than the actual time interval, which can be useful in connection with a painful activity or procedure wherein the activity/procedure is perceived to take less time than the actual time interval, or b) to be longer than the actual time interval, which can be useful in connection with a pleasant or enjoyable activity or procedure wherein the activity/procedure is perceived to occur over a longer period of time than the actual time interval.

In other embodiments, a composition composed of an effective amount of an odorant or mixture of odorants can be administered for inhalation to an individual who has an abnormal perception of time to cause their perception of time to be normalized (i.e., at or about normal) such that the individual perceives a time period to be at or about the actual time interval.

In some embodiments, administering a composition composed of an effective amount of an odorant or mixture of odorants to an individual according to the invention, can decrease or shorten the individual's perceived duration or estimate of a time period such that the time period is perceived to be shorter compared to their perception of the time period without inhalation of the odorant composition. Such an effect can be desirably used, for example, in conditions of acute pain, i.e., central line placement, bone marrow, lumbar puncture or other painful medical procedure, in social situations involving a desire for shorter perception of time as when waiting in a doctor's office, flying a long distance, or waiting in a long line at the motor vehicle department, or other situation in which an individual is required to wait and considers the time interval to be longer than the actual interval of time, in order to reduce perception of the time interval. In an exemplary embodiment, a composition can be administered to an individual to inhale that comprises a coffee-based odorant as the primary or dominant odor (aroma) of the composition, solely or in a mixture of odorants, to decrease the individual's subjective perception (estimation) of a period of time compared to the individual's subjective perception of the same period of time without inhaling the coffee-based odorant composition by a statistically significant amount ($p<0.05$). In another embodiment, the composition can comprise a coffee odorant as the primary/dominant odor in combination with another odorant as a secondary odor, for example, a peppermint odorant (or a vanilla odorant when administered to a female individual), for administration to an individual to decrease their estimation of time.

In other embodiments of the invention, administering a composition composed of an effective amount of an odorant or mixture of odorants to an individual can be utilized in situations in which a perceived prolongation of time is desirable, for example, when enjoying a hedonically positive sensory experience such as eating highly desired food (e.g., chocolate cake), which can be used to induce the individual to eat less resulting in a positive health effect, or in other situations in which an individual considers a time interval to be shorter than the actual interval of time. In an exemplary embodiment, a composition can be administered to an individual to inhale that comprises a baby powder odorant as the primary or dominant odor (aroma) of the composition, solely or in a mixture of odorants, to increase the individual's subjective perception of a period of time such that the time period is perceived to be longer compared to the individual's subjective perception of the same period of time without inhaling the baby powder odorant composition by a statistically significant amount ($p<0.05$). In another embodiment, the composition can comprise a baby powder odorant as the primary/dominant odor in combination with another odorant as a secondary odor, for administration to an individual to prolong or increase their estimation of time, for example, a vanilla odorant to increase time estimation in a male individual. In yet another embodiment, the composition can comprise one or more hedonistically positive odorants.

Clinical applications can include administering a composition composed of an odorant or mixture of odorants to patients suffering from Korsakoffs syndrome and Parkinson's disease, Attention-Deficit/Hyperactivity Disorder (ADHD), Huntington's disease, and/or other condition in which a patient demonstrates defective or impaired time processing in which they overestimate or underestimate the duration of time, to promote normalizing time perception in the individual.

As used herein, the term "odorant" refers to an odor-causing chemical compound or mixture of compounds that, when delivered in a gaseous or aerosol medium, can stimulate olfactory and/or trigeminal chemoreceptors in the nasal cavity and cause a physiological or psychological response. A hedonically positive odorant or odorant mixture is one to which the individual has a pleasant or positive reaction to its scent. A hedonically negative odorant or odorant mixture is one to which the individual has a repulsive or negative reaction to its scent. A hedonically neutral odorant or odorant mixture is one to which the individual has neither a positive nor negative reaction.

In a preferred embodiment, the subject individual is presented with the composition containing a suprathreshold concentration (e.g., about 25-55 decismel units) of the odorant or odorant mixture that is near but not so high as to become an irritant (trigeminal), which the individual inhales prior to or during an activity or time interval. The level or concentration of the odorant or odorant mixture within the composition and/or mode of administering the composition is sufficient to overcome competing or conflicting ambient odors that may act to nullify its effect.

An odorant is presented at a "suprathreshold" level when the decismel level or concentration of the odorant is beyond that needed to be detected by a normosmic individual. At its irritative level, the odorant quantity is so high and intense that the odorant stimulates predominantly the trigeminal nerve (for pain) rather than the olfactory nerve and, hence, is perceived as noxious or painful. The irritation threshold of the patient is the lowest concentration of the substance that causes immediate stinging or burning sensations in the nose, or stinging or lacrimation of the eye. (See, J. F. Gent, in *Clinical Measurement of Taste and Smell*, pages 107-166, H. L. Meiselman et al. (eds.), 602 pp., MacMillan, N.Y. (1986); R. L. Doty et al., *Ann. Neurol.* 25: 166-171 (1989); E. Koss et al., *Neurology* 38: 1228-1232 (1988); and R. Doty, *The Smell Identification Test: Administration Manual* 1983: 13-14, Philadelphia: Sensonics, Inc. (1983)).

If desired, prior to the administration of the odorant, the subject individual can undergo olfactory testing according to a test such as the University of Pennsylvania Smell Identification Test (UPSIT), a 40-question forced-choice, scratch-and-sniff identification test, and the Chicago Smell Test, a 3-item detection and identification test (R. Doty, The Smell Identification Test Administration Manual 1983: 13-14, Philadelphia: Sensonics, Inc. (1983); A. R. Hirsch et al., Chemical Senses 18(5): 570-571 (1993); A. R. Hirsch et al., Chemical Senses 17(5): 643 (1992)).

The subject individual can also be evaluated for olfactory capacity (e.g. loss of smell) according to an olfactory threshold test as known and used in the art. Such a test provides a precise magnitude of loss of smell and classifies the individual as normosmic, hyposmic or anosmic, which is useful in assessing the effectiveness of a particular odorant and/or the required concentration of the odorant, preferably a suprathreshold and near but below irritant level, to provide the desired effect according to the method of the invention. According to that test, an odorant substance such as butyl alcohol, phenyl ethyl alcohol, or pyridine, is combined in an odorless liquid medium to provide a series of dilutions, or binary steps, of the odorant. For each successive binary step up the dilution scale, the odorant is present, for example, at one half the concentration of the preceding step. The highest concentration of the odorant usually provides the substance at an irritant level. The individual is presented with the series of dilutions in ascending order, and is asked to compare each dilution step to at least one control stimulus, such as odorless propylene glycol.

In the art, a "normosmic" individual is one who can detect the odor of a substance without irritant sensations when the odorant is presented with the range of its average normal threshold. A "hyposmic" or "microsmic" individual has reduced capacity of the olfactory nerve being able to detect an odorant substance by its odor at a concentration, or decismel level, above that of a normosmic individual yet below its irritant concentration level. An "anosmic" individual is one who has essentially no olfactory nerve capacity being unable to detect the odor of the odorant substance, but has trigeminal nerve function, being able to detect an odorant substance by means of irritant, tingling sensations when it is present at an irritant concentration. A patient who is able to detect pyridine vapor by means of irritant, tingling sensations caused by stimulation of the trigeminal nerve, but who cannot distinguish a pyridine odor at a lower concentration without such sensation, is considered to be anosmic having no olfactory nerve sensitivity.

Ranges of the average normal threshold for various odorant substances can be found in the art, for example, Amoore and O'Neill, "Proposal for Unifying Scale to Express Olfactory Thresholds and Odor Levels: The "Decismel Scale"," in Proceedings of the 1988 Air Pollution control Association Annual Meeting, Paper No. 78.5 (21 pp.), Air and Waste Management Association, Pittsburgh, Pa. (1988); Amoore and Haotala, "Odor as an Aid to Chemical Safety: Odor Thresholds Compared with Threshold Limit Values and Volatiles for 214 Industrial Chemicals in Air and Water Dilution," J. Appl. Toxicology 3(6):272-290 (1983).

A suprathreshold amount is a concentration of the odorant/odorant mixture that is greater than the average normal threshold concentration of the odorant or mixture. The normal threshold concentration can be determined by administering a series of the same concentrations of the odorant/odorant mixture to a control group of at least 25 individuals who do not have a chemosensory dysfunction, and calculating the mean threshold concentration detected by the group of 25 individuals. Another alternative is to refer to the known threshold concentration value for the odorant/odorant mixture that has been established previously and published by J. Amoore et al., *J. Appl. Toxicology*, 3:272 (1983).

Odor thresholds can be expressed on the decismel scale. The decismel scale can be constructed by setting the mean threshold concentration of a chemosensory agent detected by the control group of 20 year olds at the "0" value. A decismel can be calculated by dividing the concentration of the odorant detected by the patient by the normal threshold concentration (using the published value or empirically determining the value) and then taking the logarithm of the quotient. The logarithm of the quotient can then be multiplied by 20 to obtain the decismel value. Decismel values can be positive or negative. A positive decismel value indicates the patient is less sensitive to the odorant, i.e. has a higher threshold detection concentration. A negative decismel value indicates that the patient is more sensitive to the compound, i.e. has a lower threshold detection concentration. An increase in the threshold concentration value over the mean threshold concentration value of 2 fold corresponds to 6 decismels (or ds). Determination of decismel units is known in the art, as addressed, for example, in U.S. Pat. Nos. 5,380,765 and 5,492,934 (Hirsch).

In another aspect, the invention provides compositions containing an effective amount of an odorant or mixture of odorants such that, when inhaled by an individual, the perception and/or estimation of a time interval or duration by the individual is substantially modified (i.e., increased or decreased) compared to their perception of the time interval without inhalation of the odorant composition ("control"). In some embodiments, the individual can inhale an inactive odorant or neutral odorant as a control odorant composition. Elmes et al., Adequacy of Control Comparisons in Olfactory Experiments. *Chem. Percept.* 1:247-252 (2008). Depending on the nature of the odorant composition, such an effect on an individual's perception of a time interval or duration can be objectively assessed and measured, for example, by the estimate of a defined time interval or period (e.g., 5, 30, 60, etc., seconds, minutes, etc.) when estimated by the individual with and without administration of the odorant composition.

The concentration of the odorant or mixture of odorants is preferably at a suprathreshold concentration and preferably near but not an irritant concentration at a decismel level of about 25-55 decismel units, preferably greater than 25 decismel units, preferably at about 30-55 decismel units.

In an exemplary embodiment, the composition contains an effective amount of a coffee odorant as the dominant (primary) odor or essence to cause a decrease in an individual's perception or estimate of a time period when inhaled by the individual compared to the individual's perception or estimate of the time period without inhaling the coffee odorant composition. A preferred odorant composition for use in decreasing an individual's perception of time is a formulation in which the dominant odorant component is a coffee odorant and eliminates odorants and other components that compete with the coffee odorant accords or notes to provide a full effect on the individual inhaling the odorant composition.

In another exemplary embodiment, the composition contains an effective amount of a baby powder odorant as the dominant (primary) odor or essence to cause an increase in an individual's perception or estimate of a time period when inhaled by the individual compared to the individual's perception or estimate of the time period without inhaling the baby powder odorant composition. A preferred odorant composition for use in increasing an individual's perception of time is a formulation in which the dominant odorant component is a baby powder odorant and eliminates odorants and other components that compete with the baby powder odorant accords or notes to provide a full effect on the individual inhaling the odorant composition.

The odorant or odorant mixture is provided as a formulated composition of a single essential odorant or a blend (mixture) of the essential odorants to cause the desired effect, and eliminates odorants and other components that compete with or mask the effective odorant(s). The odorant or odorant blend composition can be administered in combination with an odorless carrier such as mineral oil or water, and odorless additives such as preservatives and the like. The odorant composition can be formulated with a viscosity effective to allow for aerosolization or to provide a thick gel or cream.

In one embodiment, the composition can consist essentially of a suprathreshold and non-irritant concentration of one or more odorants such that, when inhaled by an individual, the composition is effective to modify (increase or decrease) the estimate or perception of the individual of a time interval by a statistically significant amount compared to the individual's estimate or perception of the time interval without inhalation of the composition. For example, the composition can consist essentially of a coffee odorant in a carrier with optional additives, such that, when inhaled by an individual, the composition is effective to decrease the individual's perception (or estimate) of a set time period by a statistically significant amount compared to the individual's perception (or estimate) of the same time period without inhaling the composition. In another example, the composition can consist essentially of a baby powder odorant in a carrier with optional additives, such that, when inhaled by an individual, the composition is effective to increase the individual's perception (or estimate) of a set time period by a statistically significant amount compared to the individual's perception (or estimate) of the same time period without inhaling the composition. In another example, the composition can be composed of a mixture of odorants in a carrier with optional additives, including a suprathreshold and non-irritant concentration of a coffee odorant in combination with a less than suprathreshold concentration of one or more odorants that complement and do not mask the coffee odorant, for example, a peppermint odorant, such that, when inhaled by an individual, the composition is effective to decrease the individual's perception (or estimate) of a time interval by a statistically significant amount. In yet another example, the composition can be composed of a mixture of odorants in a carrier with optional additives, including a suprathreshold and non-irritant concentration of a baby powder odorant in combination with a less than suprathreshold concentration of one or more odorants that complement and do not mask the baby powder odorant, for example, a vanilla odorant, such that, when inhaled by an individual, the composition is effective to increase the individual's perception (or estimate) of a time interval by a statistically significant amount.

Odorants for use in the present methods, are commercially available as a liquid, essential oil, extract, or other form from a variety of sources, including, for example, Energy Essentials, AromaTech, Inc. (Somerville, N.J.), Florasynth, Inc. (Teterboro, N.J.), International Flavors and Fragrances, Inc. (IFF; New York, N.Y.), among others.

The odorant composition is preferably formulated as a liquid solution or a spray, but can also be provided in the form of a cream, lotion, or other consistency, and can be contained within a liquid pump device, aerosol or non-aerosol spray device, lidded container, a blister pack, or other suitable vessel such as those known and used in the art. The odorant composition can also be contained in a solid form within a capped vessel or other closed container. It is preferred that the odorant composition is provided in a portable dispenser that is easily transportable and readily accessible by the user.

In conducting the method of the invention, the odorant composition is administered for inhalation by the subject individual. Such administration can be achieved by bringing an effective amount and concentration of the odorant composition into proximity of the individual for inhalation, for example, by spraying, by applying the odorant composition to a piece of clothing of the individual or directly to the face of the individual below the nostrils, or to a cloth or paper material such as a mask (e.g., a surgical mask, dust-type mask, earloop face mask, and the like) that is then secured over the nostrils of the subject individual, among other techniques. In another embodiment, the composition can be administered by means of a flexible laminate material (e.g., patch) sized to fit beneath the nose that incorporates the odorant composition and has a pressure-sensitive adhesive layer (covered by a release layer) that allows the material to adhere to skin and which is positioned under the nostrils of the individual, as described, for example in U.S. Pat. No. 6,769,428 (Cronk). In yet another embodiment, the odorant composition can be administered through the use of a portable delivery device operable to provide continuous delivery of a vaporous emission of the odorant composition through cannulla (tubes) inserted into the nostrils of the individual as described, for example, in U.S. Pat. No. 6,803,987 (Mamie). Other delivery systems can be used for delivery of the odorant composition to the individual.

Odorants or odorant mixtures can be readily screened and assessed for effectiveness in modifying and/or improving (e.g., normalizing) an individual's perception of time according to the invention. For example, a composition containing an odorant or mixture of odorants can be administered to an individual for inhalation to evaluate its effect on modifying their subjective perception (judgment) or estimation of a time interval, for example, which can be manifested by a decrease or an increase in the individual's subjective judgment or the individual's estimate of the time interval compared to their subjective judgment or estimation of the same time interval without inhaling the odorant composition. For example, an individual can be asked to subjectively judge or provide an estimate of (e.g., in seconds) the duration (length) of time between two events, such as the presentations of two consecutive tones at a set time interval without inhaling the test odorant composition or, in other embodiments, inhaling a neutral or inactive odorant composition ("control"). The subject can then inhale a test odorant composition, and two consecutive tones can again be presented at the set time interval, and the subject asked to make a subjective judgment as to whether the duration between the second pair of tones was shorter or longer than the time interval between the first pair of tones (the control) or make an estimate of the time interval (e.g., in seconds). Optionally, the individual can be questioned as to a positive or negative reaction to the pleasantness of the scent to assess the hedonics of the odorant composition to the individual.

Another embodiment of a method of screening a composition formulated with an odorant or a mixture of odorants for effectively altering an individual's perception of time can comprise the steps of:

a) having an individual estimate a set time interval (for example, a 60-second interval) without inhalation of the target odorant composition as a "control score";

b) having the individual inhale a suprathreshold but non-irritant concentration of a composition consisting essentially of the odorant or odorants to be tested, and then estimate the same set time interval from step a), and then tallying the score to provide a "test score";

c) comparing the control score to the test score to determine the statistical significance between the two scores; and e) eliminating the odorant or odorant mixture as being ineffective to modify the individual's perception of time if not statistically significant ($p<0.05$).

The screening test as well as the method of the invention can include other steps such as having the inhaling individual identify the composition as hedonically positive, neutral or negative, and testing olfactory ability and/or olfactory capacity of the individual, among other olfactory tests known and used in the art.

According to the invention, a composition comprising the odorant or odorant mixture is administered (e.g., dispensed) as a vaporous emission to the nostrils of an individual for inhalation of a concentration of a primary odorant or odorant mixture effective to modify the individual's perception of time, for example, using a coffee odorant-based composition to decrease the individual's perception of time, or using a baby powder odorant-based composition to increase the individual's perception of time. Such an effect can be assessed and measured objectively by comparing the individual's subjective judgment or the individual's estimation of a set time period with and without the administration of the odorant composition.

The odorant composition can be packaged as part of an article of manufacture, or kit. In one embodiment, the article of manufacture can comprise a container of an odorant composition or, packaged together, a container of a first odorant and a container of a second odorant (etc.) for combining together to form the odorant composition. The odorant composition comprises an odorant or mixture of odorants in a suprathreshold and but non-irritant concentration, and preferably near a non-irritant concentration, effective to substantially modify an individual's perception of time when administered according to the method of the invention.

In a preferred embodiment, the composition consists essentially of a coffee odorant. For example, the article of manufacture can comprise a container of an odorant composition consisting essentially of a coffee odorant or of one or more odorants of which a coffee odorant is the dominant odor or essence, or in another embodiment, a container of an odorant composition consisting essentially of a baby powder odorant or of one or more odorants of which a baby powder odorant is the dominant odor or essence. The article of manufacture can further include a device for use in delivery of the composition to a subject individual, for example, a mask for placement over the nose of the individual, a device for applying the composition directly to the skin under the nostrils of the individual, a spray delivery device, among others.

The kit can further include one or more elements for testing the individual, that can be separately packaged, including a device for administering odorant(s) for testing olfactory ability of the individual (e.g., UPSIT), and/or a device for administering a series of odorants for testing olfactory threshold of the individual (e.g., pyridine dilution series).

The article of manufacture can further comprise written or other format of instructions (e.g., C.D., video, cassette tapes, etc.) for use of the odorant composition for modifying an individual's perception of time in a method according to the invention, including decreasing their perception of time, or in other embodiments, increasing their perception of time. In another embodiment, the article of manufacture can comprise packaging material and an odorant composition according to the invention contained within the packaging material, wherein the packaging material comprises a label that indicates that the odorant composition can be used for modifying (i.e., increasing or decreasing) perception of time. The article of manufacture can also include an odorant composition and instructions for testing olfactory threshold according methods known in the art. The parts of the article of manufacturing can be contained or separately packaged within a packaging material, such as a box, bag, pouch, and the like.

The invention will be further described by reference to the following detailed example. This example is not meant to limit the scope of the invention that has been set forth in the foregoing description. Variation within the concepts of the invention is apparent to those skilled in the art. The disclosures of the cited references throughout the application are incorporated by reference herein.

EXAMPLE

Methods. Twenty nonsmokers (19 males, 1 female, average age of 34 years old, and age range of 28 to 43 years)

participated in this institutional review board (IRB) approved study. None of the subjects suffered from asthma or unusual smell sensitivity, and none were pregnant. All subjects perceived that they had a normal sense of smell. All subjects scored 3/3 on the Quick Smell Identification Test (Q-SIT), a scratch and sniff smell identification test (Sensonics, Inc., Haddon Heights, N.J.), consistent with normosmia.

In a single-blind experimental design, all subjects underwent three one-minute epochs of time estimation while wearing a 3M™ Aseptex™ molded surgical mask impregnated with custom essence Columbian Coffee CE-44553 aroma (International Flavors and Fragrances, Inc., New York, N.Y.), Baby Powder 3169-HS aroma (IFF), or no aroma.

Subjects were randomly assigned as to the order of the six different permutations of masks presentations, as follows:
(1) coffee, blank, baby powder
(2) coffee, baby powder, blank
(3) baby powder, coffee, blank
(4) baby powder, blank, coffee
(5) blank, coffee, baby powder
(6) blank, baby powder, coffee After placement of a mask, a 10-second interval elapsed before timing began. Subjects were left alone in the room without a time keeping device, and asked to indicate when they perceived 60 seconds had elapsed. Subjects underwent a no-odor, one-minute wash out interval before a new mask was introduced. The Hawthorn effect was minimized by removing the Examiner from the room during estimation of time perception so that subjects would not be able to use the Examiner's body language to estimate time. After testing, subjects were queried regarding familiarity of the odor and asked to identify it, and regarding the hedonics (pleasant versus unpleasant) of the odor. Repeated measures analysis of variance was used to test for differences in time perception across the three exposures and specifically to compare exposure to Columbian coffee and baby powder to the blank mask, using significance criteria $p<0.05$. Order of presentation was included as a covariate in the model to check the effect of odors independent of order, treating order as both an six-level factor and a three-level factor indicating which odor is presented first. Hedonics and familiarity were considered by performing a sensitivity analysis excluding subjects unfamiliar with baby powder or who dislike coffee.

Results/Discussion. The results are shown in Table 1. Statistical significance was determined for perception of time for the group as a whole with positive hedonics to coffee and those with positive familiarity toward the baby powder. Perception of 60 seconds was significantly different across the three exposure groups ($p.<0001$). There was no significant interaction between effect of exposures and order of presentation. Hedonically positive Columbian coffee aroma induced subjects to perceive 60 seconds to be shorter whereas hedonically negative baby powder aroma induced subjects to estimate longer time for a 60 second interval. The Columbian coffee aroma (odorant) reduced the estimated duration of the 60-second interval by 8.6 seconds ($p=0.0123$). The baby powder aroma (odorant) increased estimated duration of the 60-second interval by 34.3 seconds ($p<0.0001$). These effects were both still significant adjusted for order of presentation ($p=0.0086$ and $p<0.01$ adjusting for six different orders of three exposures; $p=0.0167$ and $p<0.0001$ adjusting for which odor was presented first). FIG. 1 illustrates the mean time (in seconds) of perception of the 60-second interval across the 20 subjects for the coffee and baby powder odorants (56.3 seconds and 99.3 seconds, respectively) and the blank mask (65 seconds).

Eighteen (18) of the 20 subjects (90%) reported positive hedonics and 100% of the subjects described familiarity for the coffee odorant. None of the subjects had positive hedonics toward the baby powder odorant, and 18 of the 20 subjects found the baby powder odorant to be familiar.

Sub-analyses were performed that excluded those subjects who found the baby powder odorant to be unfamiliar and the subjects who disliked the coffee odorant (n=16). In the subgroup, the coffee odorant decreased perceived perception of time by 9.4 seconds ($p=0.0199$) and the baby powder odorant increased time perception by 32.9 seconds ($p<0.0001$).

TABLE 1

| | | Time reported exposed to: | | | Exclusion | | | |
| --- | --- | --- | --- | --- | --- | --- | --- | --- |
| ID | Age | Coffee t_coff | Baby Powder t_bp | Blank Mask t_noar | Criteria: bp_nfam | cof_disl | order | first |
| 1 | 34 | 54 | 106 | 72 | 0 | 0 | 1 | 1 |
| 2 | 31 | 85 | 91 | 84 | 0 | 0 | 1 | 1 |
| 3 | 36 | 87 | 111 | 78 | 0 | 0 | 1 | 1 |
| 4 | 43 | 62 | 107 | 65 | 0 | 0 | 1 | 1 |
| 5 | 35 | 51 | 72 | 75 | 0 | 0 | 2 | 1 |
| 6 | 35 | 63 | 94 | 79 | 0 | 0 | 2 | 1 |
| 7 | 33 | 51 | 129 | 84 | 0 | 0 | 2 | 1 |
| 8 | 30 | 50 | 75 | 49 | 0 | 0 | 3 | 2 |
| 9 | 28 | 40 | 85 | 34 | 0 | 0 | 3 | 2 |
| 10 | 28 | 39 | 86 | 63 | 0 | 0 | 3 | 2 |
| 11 | 37 | 46 | 113 | 69 | 0 | 1 | 4 | 2 |
| 12 | 41 | 55 | 98 | 56 | 0 | 0 | 4 | 2 |
| 13 | 30 | 50 | 128 | 58 | 1 | 0 | 4 | 2 |
| 14 | 39 | 37 | 108 | 66 | 0 | 0 | 5 | 3 |
| 15 | 38 | 66 | 88 | 50 | 0 | 0 | 5 | 3 |
| 16 | 28 | 51 | 92 | 71 | 0 | 0 | 5 | 3 |
| 17 | 30 | 75 | 79 | 71 | 0 | 1 | 6 | 3 |
| 18 | 32 | 68 | 102 | 63 | 1 | 0 | 6 | 3 |
| 19 | 29 | 57 | 121 | 65 | 0 | 0 | 6 | 3 |
| 20 | 42 | 39 | 101 | 47 | 0 | 0 | 6 | 3 |
| Means | | 56.3 | 99.3 | 65.0 | | | | |
| SDs | | 14.3970026 | 16.38388168 | 13.0362854 | | | | |
| | | Coffee | Baby Powder | Blank Mask | | | | |

The results demonstrated that an individual's perception of time can be modified by administering an odorant independent of the hedonics of the odorant to the individual. The results further demonstrated that inhalation of a coffee odorant had a statistically significant effect on decreasing an individual's perception of a time duration, and a baby powder odorant had a statistically significant effect on increasing an individual's perception of a time duration. Administration of the Columbian coffee odorant reduced estimation of time duration whereas the baby powder increased estimation of time duration, that is, administration of the coffee odorant speeded up time perception whereas the baby powder odorant (aroma) slowed down perception of time. Increased perceived speed of time is known as telescoping while the slowing of time is described as time dilation or chronostasis.

The exact mechanism was not determined. Although not intended to limit the invention, a possible mechanism by which an odorant may have end effect is through inclusion of cerebral processes involved in time perception. Time perception involves the basal ganglia, cerebellum, and the right inferior parietal regions. Projections from the olfactory bulb have been identified in these regions. Thus, olfactory projections may have acted on those neural pathways effecting time perception.

An aroma's influence on affect modulation may be a controlling factor. Aromas through their direct impact on the limbic system or through effect on induction of memory may have predisposed subjects to a specific affective state. In particular, odor hedonic and affect congruence can induce a positive or negative effect. For example, Columbian coffee aroma, which was universally viewed as pleasant, may induce a positive affective state such as happiness, positive memories and thus distraction, which then can caused the perceived time to pass more quickly. Alternatively, most subjects disliked baby powder aroma, and aromas viewed as unpleasant have been shown to induce a negative affect. The baby powder odor may have induced a negative affective state in subject, which then may have been manifested as emotions such as anger, irritability, and impatience, which occur when in a negative mood state, which may have influenced the subjects to slow down their perception of time, such that the time interval was perceived to be longer than actual. Alternatively the Columbian coffee odorant may have induced a Pavlovian conditioned response of drinking coffee and associated caffeine effects, to cause subjects to be more awake, anxious and alert, such that the individual perceived that time is moving faster. The baby powder odorant may have facilitated a relaxed effect which then induces subjects into a pre-sleep experience, with a subjective perception of time slowing down.

In compliance with the statute, the invention has been described in language more or less specific as to structural and methodical features. It is to be understood, however, that the invention is not limited to the specific features shown and described, since the means herein disclosed comprise preferred forms of putting the invention into effect. The invention is, therefore, claimed in any of its forms or modifications within the proper scope of the appended claims appropriately interpreted in accordance with the doctrine of equivalents. The disclosures of the cited patents, applications, and other references throughout the application are incorporated by reference herein.

What is claimed is:

1. A method of treating a person having a defective or impaired time processing condition consisting essentially of administering to the person by inhalation, therapeutically effective amounts of a vanilla extract, a peppermint extract and a coffee extract, wherein the person suffers from a disease/disorder selected from the group consisting of Korsakoff's syndrome, Parkinson's disease, Attention-Deficit/Hyperactivity Disorder and Huntington's disease.

2. A method of treating a person having a defective or impaired time processing condition consisting essentially of having the person inhale therapeutically effective amounts of a vanilla extract, a peppermint extract and a coffee extract, wherein the person suffers from a disease/disorder selected from the group consisting of Korsakoff's syndrome, Parkinson's disease, Attention-Deficit/Hyperactivity Disorder and Huntington's disease.

* * * * *